United States Patent
Han et al.

(10) Patent No.: US 10,215,698 B2
(45) Date of Patent: Feb. 26, 2019

(54) MULTIPLE LIGHT PATHS ARCHITECTURE AND OBSCURATION METHODS FOR SIGNAL AND PERFUSION INDEX OPTIMIZATION

(71) Applicant: Apple Inc., Cupertino, CA (US)

(72) Inventors: Chin San Han, Mountain View, CA (US); Ueyn Block, Menlo Park, CA (US); Brian R. Land, Woodside, CA (US); Nevzat Akin Kestelli, San Jose, CA (US); Serhan Isikman, Sunnyvale, CA (US); Albert Wang, Sunnyvale, CA (US); Justin Shi, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 927 days.

(21) Appl. No.: 14/569,235

(22) Filed: Dec. 12, 2014

(65) Prior Publication Data
US 2016/0058312 A1 Mar. 3, 2016

Related U.S. Application Data

(60) Provisional application No. 62/044,515, filed on Sep. 2, 2014.

(51) Int. Cl.
*A61B 6/00* (2006.01)
*G01N 21/47* (2006.01)
(Continued)

(52) U.S. Cl.
CPC ....... *G01N 21/4738* (2013.01); *A61B 5/0059* (2013.01); *G01N 21/55* (2013.01);
(Continued)

(58) Field of Classification Search
CPC .... A61B 2560/0475; A61B 2562/0233; A61B 5/0059; A61B 5/02416; A61B 5/681;
(Continued)

(56) References Cited

U.S. PATENT DOCUMENTS 5,246,002 A 9/1993 Prosser
5,483,261 A 1/1996 Yasutake
(Continued)

FOREIGN PATENT DOCUMENTS

CN 101108126 B 1/2008
CN 103610467 A 3/2014
(Continued)

OTHER PUBLICATIONS

European Search Report dated Jan. 21, 2016, for EP Patent Application No. 15179618,2, seven pages.
(Continued)

*Primary Examiner* — Amelie R Gillman
(74) *Attorney, Agent, or Firm* — Morrison & Foerster LLP

(57) ABSTRACT

A photoplethysmographic (PPG) device is disclosed. The PPG device can include one or more light emitters and one or more light sensors to generate the multiple light paths for measuring a PPG signal and perfusion indices of a user. The multiple light paths between each pair of light emitters and light detectors can include different separation distances to generate both an accurate PPG signal and a perfusion index value to accommodate a variety of users and usage conditions. In some examples, the multiple light paths can include the same separation distances for noise cancellation due to artifacts resulting from, for example, tilt and/or pull of the device, a user's hair, a user's skin pigmentation, and/or motion. The PPG device can further include one or more lenses and/or reflectors to increase the signal strength and/or and to obscure the optical components and associated wiring from being visible to a user's eye.

19 Claims, 13 Drawing Sheets

(51) Int. Cl.
  *G01N 21/55* (2014.01)
  *A61B 5/00* (2006.01)
  *A61B 5/024* (2006.01)

(52) U.S. Cl.
  CPC .......... *A61B 5/02416* (2013.01); *A61B 5/681* (2013.01); *A61B 5/6898* (2013.01); *A61B 5/7203* (2013.01); *A61B 2560/0475* (2013.01); *A61B 2562/0233* (2013.01); *G01N 2201/062* (2013.01); *G01N 2201/068* (2013.01); *G01N 2201/0638* (2013.01)

(58) Field of Classification Search
  CPC .............. A61B 5/6898; A61B 5/7203; G01N 21/4738; G01N 21/55; G01N 2201/062; G01N 2201/0638; G01N 2201/068
  See application file for complete search history.

(56) References Cited

U.S. PATENT DOCUMENTS

| | | |
|---|---|---|
| 5,488,204 A | 1/1996 | Mead et al. |
| 5,782,237 A | 7/1998 | Casciani et al. |
| 5,825,352 A | 10/1998 | Bisset et al. |
| 5,835,079 A | 11/1998 | Shieh |
| 5,880,411 A | 3/1999 | Gillespie et al. |
| 6,188,391 B1 | 2/2001 | Seely et al. |
| 6,310,610 B1 | 10/2001 | Beaton et al. |
| 6,323,846 B1 | 11/2001 | Westerman et al. |
| 6,594,513 B1* | 7/2003 | Jobsis ................ A61B 5/14553 600/323 |
| 6,690,387 B2 | 2/2004 | Zimmerman et al. |
| 7,015,894 B2 | 3/2006 | Morohoshi |
| 7,184,064 B2 | 2/2007 | Zimmerman et al. |
| 7,372,778 B2 | 5/2008 | Klopfenstein et al. |
| 7,663,607 B2 | 2/2010 | Hotelling et al. |
| 7,740,589 B2 | 6/2010 | Maschke et al. |
| 8,479,122 B2 | 7/2013 | Hotelling et al. |
| 2002/0058865 A1 | 5/2002 | Cheng et al. |
| 2005/0021110 A1* | 1/2005 | Maschke ............ A61B 5/0002 607/88 |
| 2005/0083687 A1* | 4/2005 | Brass .................... G01N 21/31 362/231 |
| 2006/0197753 A1 | 9/2006 | Hotelling |
| 2008/0004510 A1 | 1/2008 | Tanzawa et al. |
| 2008/0019218 A1* | 1/2008 | Klopfenstein ..... A61B 5/02416 368/70 |
| 2009/0163775 A1 | 6/2009 | Barrett et al. |
| 2009/0326346 A1 | 12/2009 | Kracker et al. |
| 2010/0056934 A1* | 3/2010 | Cho .................. A61B 5/02416 600/502 |
| 2011/0077537 A1* | 3/2011 | Ebara .................. A61B 5/0245 600/500 |
| 2011/0112387 A1 | 5/2011 | Li et al. |
| 2011/0260176 A1 | 10/2011 | Onoe et al. |
| 2013/0041268 A1 | 2/2013 | Rimoldi et al. |
| 2013/0046192 A1 | 2/2013 | Lin et al. |
| 2013/0131519 A1* | 5/2013 | LeBoeuf .............. A61B 5/0077 600/476 |
| 2013/0324866 A1* | 12/2013 | Gladshtein ........... A61B 5/0059 600/507 |
| 2015/0065830 A1* | 3/2015 | Karp .................... A61B 5/7221 600/331 |
| 2016/0235369 A1* | 8/2016 | Horikawa ............ A61B 5/7214 |

FOREIGN PATENT DOCUMENTS

| | | |
|---|---|---|
| EP | 1 946 697 A1 | 7/2008 |
| JP | 57-93039 A | 6/1982 |
| JP | 02-031734 A | 2/1990 |
| JP | H-09-508291 A | 8/1997 |
| JP | 11-128184 A | 5/1999 |
| JP | 2000-163031 A | 6/2000 |
| JP | 2002-342033 A | 11/2002 |
| JP | 2002-345760 A | 12/2002 |
| JP | 2003-508143 A | 3/2003 |
| JP | 2005-040608 A | 2/2005 |
| JP | 2008-264302 A | 11/2008 |
| JP | 2009-533121 A | 9/2009 |
| JP | 2011-251007 A | 12/2011 |
| JP | 2013-094482 A | 5/2013 |
| JP | 2013-118922 A | 6/2013 |
| JP | 2013-536001 A | 9/2013 |
| WO | WO-95/20757 A1 | 8/1995 |
| WO | WO-01/17420 A1 | 3/2001 |
| WO | WO-2007/122375 A2 | 11/2007 |
| WO | WO-2009/139029 A1 | 9/2011 |
| WO | WO-2012/011029 A1 | 1/2012 |
| WO | WO-2014/066791 A1 | 5/2014 |
| WO | WO-2015/084375 A1 | 6/2015 |
| WO | WO-2015/122980 A1 | 8/2015 |

OTHER PUBLICATIONS

ROC (Taiwan) Search Report dated Jan. 23, 2017, for TW Patent Application No. 104126881, with English translation, two pages.

Lee, S.K. et al. (Apr. 1985). "A Multi-Touch Three Dimensional Touch-Sensitive Tablet," *Proceedings of CHI: ACM Conference on Human Factors in Computing Systems*, pp. 21-25.

Rubine, D.H. (Dec. 1991). "The Automatic Recognition of Gestures," CMU-CS-91-202, Submitted in Partial Fulfillment of the Requirements for the Degree of Doctor of Philosophy in Computer Science at Carnegie Mellon University, 285 pages.

Rubine, D.H. (May 1992). "Combining Gestures and Direct Manipulation," CHI ' 92, pp. 659-660.

Westerman, W. (Spring 1999). "Hand Tracking, Finger Identification, and Chordic Manipulation on a Multi-Touch Surface," A Dissertation Submitted to the Faculty of the University of Delaware in Partial Fulfillment of the Requirements for the Degree of Doctor of Philosophy in Electrical Engineering, 364 pages.

Chinese Search Report dated Sep. 20, 2017, for CN Application No. 201510540493.2, with English translation, four pages.

\* cited by examiner

| Light Path | Light Emitter | Light Sensor | Path Length (mm) | PPG Signal | Perfusion Index |
|---|---|---|---|---|---|
| 625 | 616 | 614 | 4.944 | 1.11 | 0.96 |
| 621 | 606 | 604 | 5.444 | 0.75 | 1.10 |
| 623 | 606 | 614 | 5.915 | 0.51 | 1.23 |
| 627 | 616 | 604 | 6.543 | 0.31 | 1.39 |

| Light Path | Light Emitter | Light Sensor | Separation Distance |
|---|---|---|---|
| 721 | 706 | 704 | d1 |
| 723 | 706 | 734 | d3 |
| 725 | 706 | 714 | d4 |
| 727 | 716 | 734 | d2 |
| 729 | 716 | 714 | d1 |
| 731 | 716 | 724 | d3 |
| 733 | 716 | 704 | d4 |
| 735 | 706 | 724 | d2 |

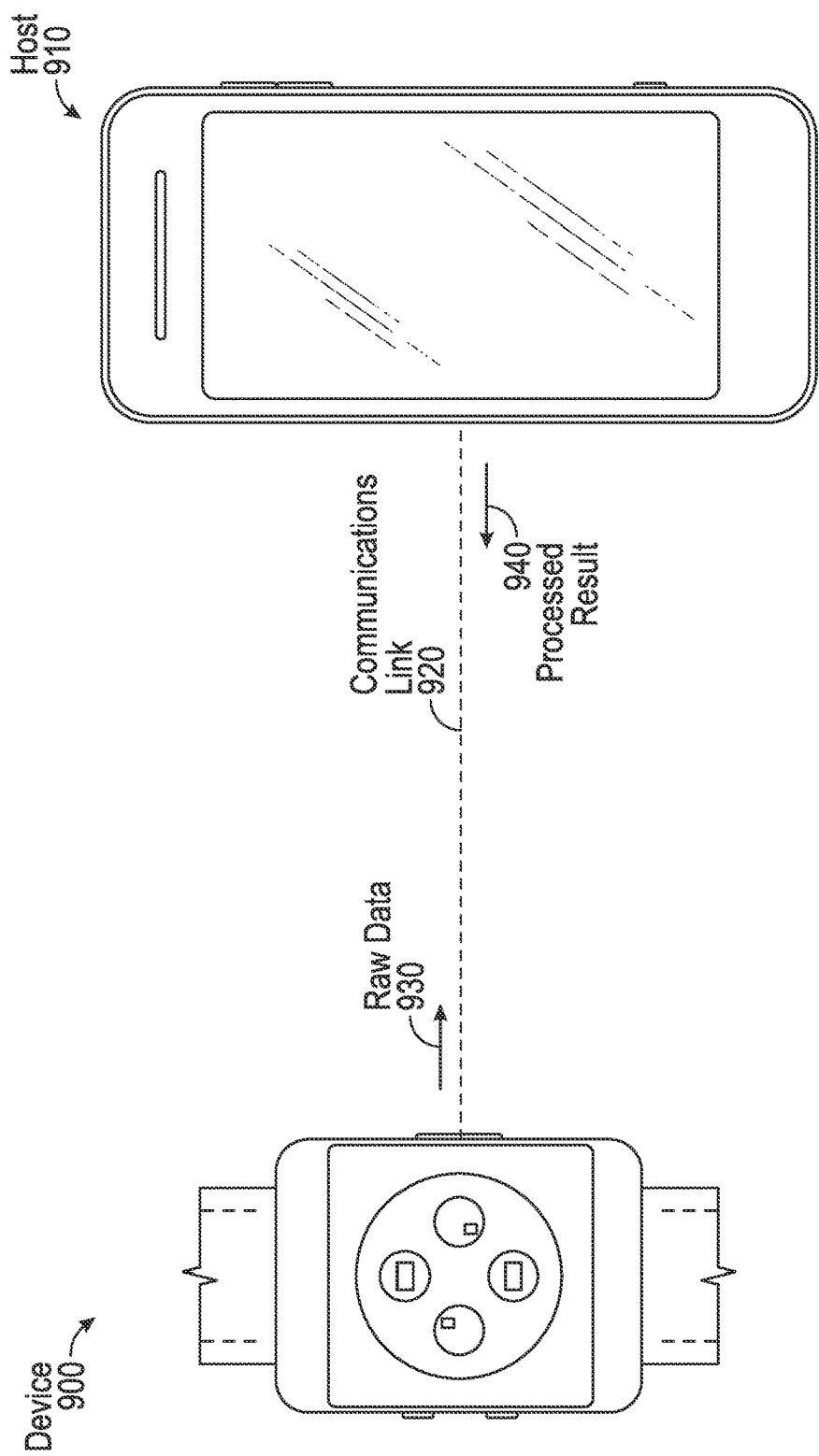

MULTIPLE LIGHT PATHS ARCHITECTURE AND OBSCURATION METHODS FOR SIGNAL AND PERFUSION INDEX OPTIMIZATION

FIELD

This relates generally to a device that measures a photoplethysmographic (PPG) signal, and, more particularly, to architectures for multiple light paths and obscuration methods for PPG signal and perfusion index optimization.

BACKGROUND

A photoplethysmographic (PPG) signal can be measured by PPG systems to derive corresponding physiological signals (e.g., pulse rate). In a basic form, PPG systems can employ a light source or light emitter that injects light into the user's tissue and a light detector to receive light that reflects and/or scatters and exits the tissue. The received light includes light with an amplitude that is modulated as a result of pulsatile blood flow (i.e., "signal") and parasitic, non-signal light with an amplitude that can be modulated (i.e., "noise" or "artifacts") and/or unmodulated (i.e., DC). Noise can be introduced by, for example tilt and/or pull of the device relative to the user's tissue, hair, and/or motion.

For a given light emitter and light detector, the PPG pulsatile signal (i.e., detected light modulated by pulsatile blood flow) can decrease as the separation distance between the light emitter and light detector increases. On the other hand, perfusion index (i.e., the ratio of pulsatile signal amplitude versus DC light amplitude) can increase as the separation distance between the light emitter and light detector increases. Higher perfusion index tends to result in better rejection of noise due to motion (i.e., rejection of motion artifacts). Therefore, shorter separation distances between a light emitter and a light sensor can favor high PPG signal strength, while longer separation distances can favor high perfusion index (e.g., motion performance). That is, a trade-off can exist, making it difficult to optimize separation distance for particular user skin/tissue types and usage conditions.

Additionally, the PPG system can include several light emitters, light detectors, components, and associated wiring that may be visible to a user's eye, making the PPG system aesthetically unappealing.

SUMMARY

This relates to a PPG device configured with an architecture suitable for multiple light paths. The architecture can include one or more light emitters and one or more light sensors to generate the multiple light paths for measuring a PPG signal and a perfusion index of a user. The multiple light paths (i.e., the optical paths formed between each pair of light emitter and light detector) can include different locations and/or emitter-to-detector separation distances to generate both an accurate PPG signal and perfusion index value to accommodate a variety of users and a variety of usage conditions. In some examples, the multiple light paths can include different path locations, but the same separation distances along each path. In other examples, the multiple light paths can include overlapping, co-linear paths (i.e., along the same line) but with different emitter-to-detector separation distances along each path. In other examples, the multiple light paths can include different path locations and different emitter-to-detector separation distances along each path. In such examples, the particular configuration of the multiple light paths can be optimized for cancellation of noise due to artifacts resulting from, for example, tilt and/or pull of the device, a user's hair, a user's skin pigmentation, and/or motion. The PPG device can further include one or more lenses and/or reflectors to increase the signal strength and/or and to obscure the light emitters, light sensors, and associated wiring from being visible to a user's eye.

BRIEF DESCRIPTION OF THE DRAWINGS

FIG. 9 illustrates an exemplary configuration in which a device is connected to a host according to examples of the disclosure.

DETAILED DESCRIPTION

Figure 1:
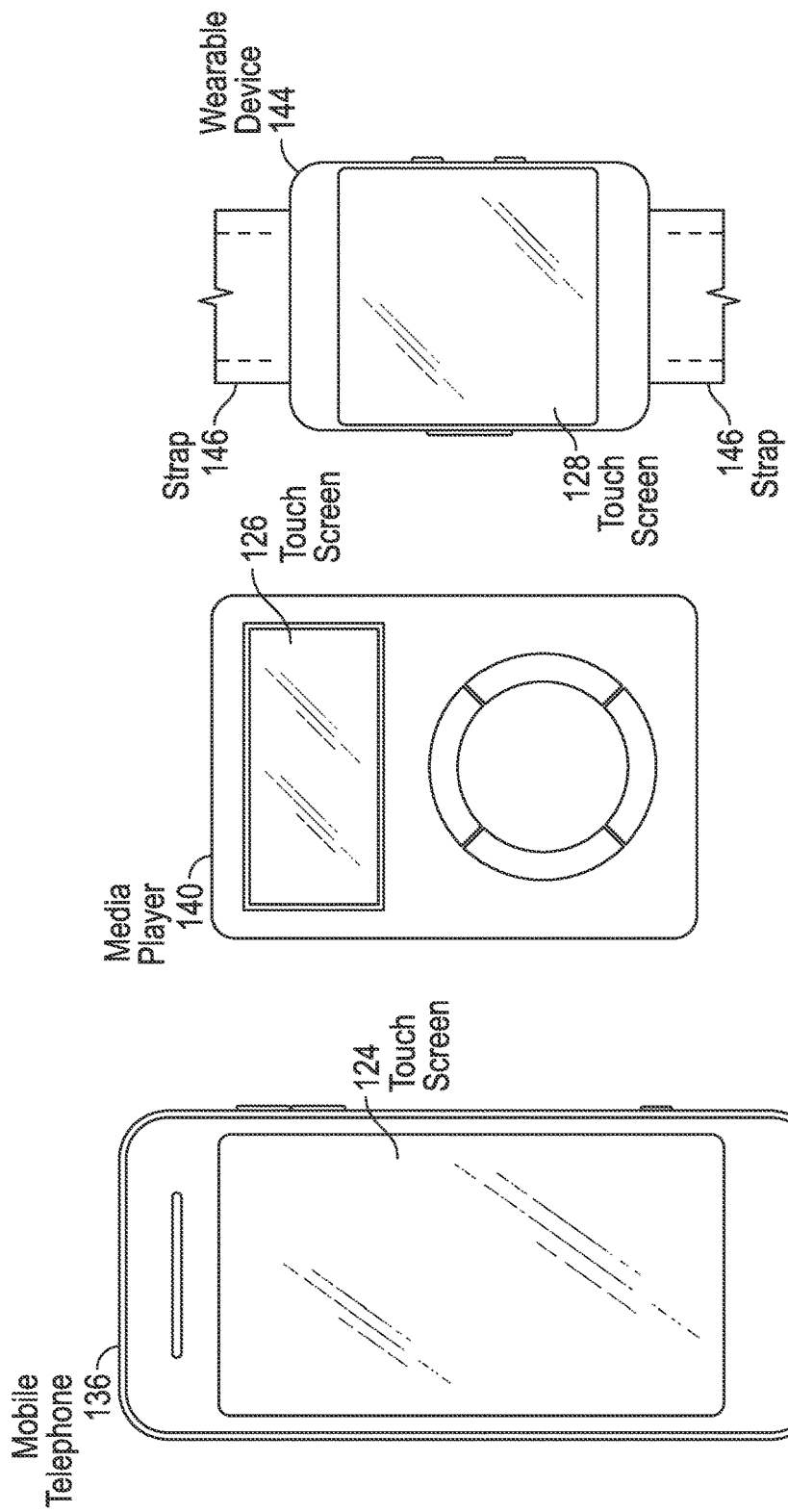
FIGS. 1A-1C illustrate systems in which examples of the disclosure can be implemented.

In the following description of examples, reference is made to the accompanying drawings in which it is shown by way of illustration specific examples that can be practiced. It is to be understood that other examples can be used and structural changes can be made without departing from the scope of the various examples.

Various techniques and process flow steps will be described in detail with reference to examples as illustrated in the accompanying drawings. In the following description, numerous specific details are set forth in order to provide a thorough understanding of one or more aspects and/or features described or referenced herein. It will be apparent, however, to one skilled in the art, that one or more aspects and/or features described or referenced herein may be practiced without some or all of these specific details. In other instances, well-known process steps and/or structures have not been described in detail in order to not obscure some of the aspects and/or features described or referenced herein.

Further, although process steps or method steps can be described in a sequential order, such processes and methods can be configured to work in any suitable order. In other words, any sequence or order of steps that can be described in the disclosure does not, in and of itself, indicate a requirement that the steps be performed in that order. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modification thereto, does not imply that the illustrated process or any of its steps are necessary to one or more of the examples, and does not imply that the illustrated process is preferred.

A photoplethysmographic (PPG) signal can be measured by PPG systems to derive corresponding physiological signals (e.g., pulse rate). Such PPG systems can be designed to be sensitive to changes in blood in a user's tissue that can result from fluctuations in the amount or volume of blood or blood oxygen contained in a vasculature of the user. In a basic form, PPG systems can employ a light source or light emitter that injects light into the user's tissue and a light detector to receive light that reflects and/or scatters and exits the tissue. The PPG signal is the amplitude of the reflected and/or scattered light that is modulated with volumetric change in blood volume in the tissue. However, the PPG signal may be compromised by noise due to artifacts. Artifacts resulting from, for example, tilt and/or pull of the device relative to the user's tissue, hair, and/or motion can introduce noise into the signal. For example, the amplitude of reflected light can modulate due to the motion of the user's hair. As a result, the amplitude modulation of the reflected light caused by hair motion can be erroneously interpreted as a result of pulsatile blood flow.

This disclosure relates to a multiple light paths architecture and obscuration methods for PPG signal and perfusion index optimization. The architecture can include one or more light emitters and one or more light sensors to generate the multiple light paths to measure a PPG signal and a perfusion index of a user. The multiple light paths can include different locations and/or separation distances between light emitters and light detectors to generate both an accurate PPG signal and perfusion index value to accommodate a variety of users and a variety of usage conditions. In some examples, the multiple light paths can include different path locations, but the same emitter-to-detector separation distances along each path. In some examples, the multiple light paths can include overlapping, co-linear paths (i.e., along the same line), but with different emitter-to-separation distances along each other. In some examples, the multiple light paths can include different path locations and different emitter-to-detector separation distances along each path. In such examples, the particular configuration of the multiple light paths is optimized for noise cancellation due to artifacts such as tilt and/or pull of the device, a user's hair, a user's skin pigmentation, and/or motion. In some examples, the device can include one or more lenses and/or reflectors to increase the signal strength and/or to obscure the light emitters, light sensors, and associated wiring from being visible to a user's eye.

Representative applications of methods and apparatus according to the present disclosure are described in this section. These examples are being provided solely to add context and aid in the understanding of the described examples. It will thus be apparent to one skilled in the art that the described examples may be practiced without some or all of the specific details. In other instances, well-known process steps have been described in detail in order to avoid unnecessarily obscuring the described examples. Other applications are possible, such that the following examples should not be taken as limiting.

FIGS. 1A-1C illustrate systems in which examples of the disclosure can be implemented. FIG. 1A illustrates an exemplary mobile telephone 136 that can include a touch screen 124. FIG. 1B illustrates an exemplary media player 140 that can include a touch screen 126. FIG. 1C illustrates an exemplary wearable device 144 that can include a touch screen 128 and can be attached to a user using a strap 146. The systems of FIGS. 1A-1C can utilize the multiple light path architectures and obscuration methods as will be disclosed.

Figure 2:
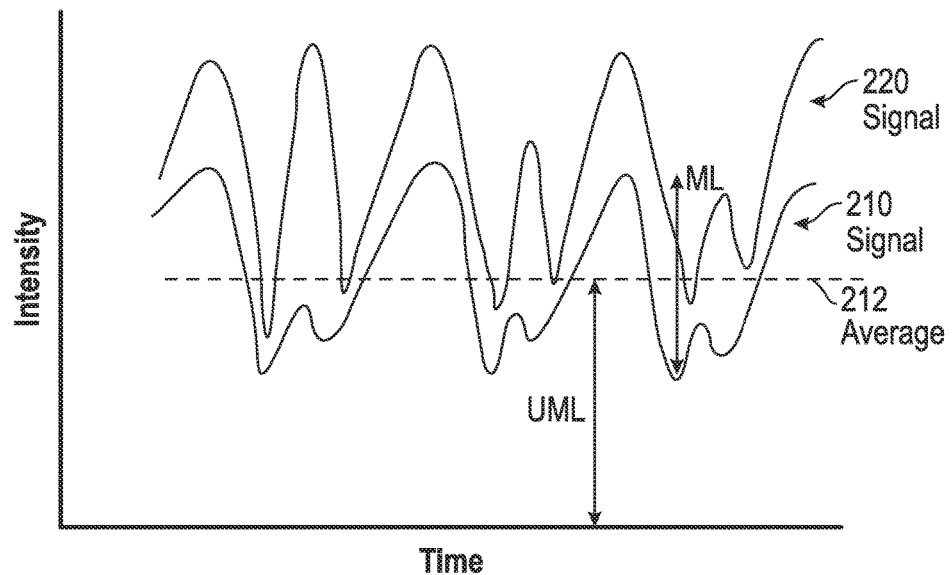
FIG. 2 illustrates an exemplary PPG signal.

FIG. 2 illustrates an exemplary PPG signal. A user's PPG signal absent of artifacts is illustrated as signal 210. However, movement of the body of the user can cause the skin and vasculature to expand and contract, introducing noise to the signal. Additionally, a user's hair and/or tissue can change the amplitude of light reflected and the amplitude of light absorbed. A user's PPG signal with artifacts is illustrated as signal 220. Without extraction of noise, signal 220 can be misinterpreted.

Signal 210 can include light information with an amplitude that is modulated as a result of pulsatile blood flow (i.e., "signal") and parasitic, unmodulated, non-signal light (i.e., DC). From the measured PPG signal 210, a perfusion index can be determined. The perfusion index can be the ratio of received modulated light (ML) to unmodulated light (UML) (i.e., ratio of blood flow modulated signal to static, parasitic DC signal) and can give extra information regarding the user's physiological state. The modulated light (ML) can be the peak-to-valley value of signal 210, and unmodulated light (UML) can be the zero-to-average (using average 212) value of signal 210. As shown in FIG. 2, the perfusion index can be equal to the ratio of ML to UML.

Both the PPG signal and perfusion index can be related to an accurate measurement of physiological signals such as heart rate. However, the PPG signal can include noise from modulated light resulting from, for example, motion of the user's tissue and/or the PPG device. Higher perfusion index (e.g., higher pulsatile signal and/or lower parasitic DC) can result in better rejection of such motion noise. Additionally, the intensity of a PPG signal relative to perfusion index can vary for different users. Some users may naturally have a high PPG signal, but a weak perfusion index or vice versa. Thus, the combination of PPG signal and perfusion index can be used to determine physiological signals for a variety of users and a variety of usage conditions.

Figure 3A:
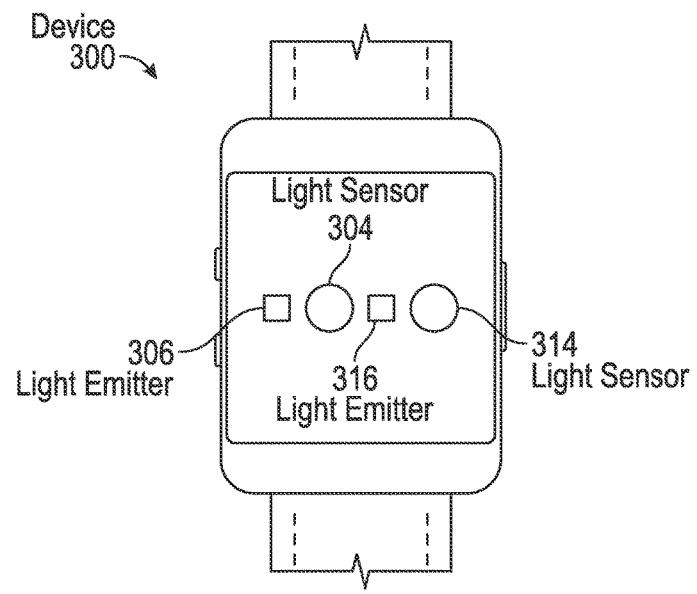
FIG. 3A illustrates a top view and FIG. 3B illustrates a cross-sectional view of an exemplary electronic device including light sensors and light emitters for determining a heart rate signal.
Figure 3B:
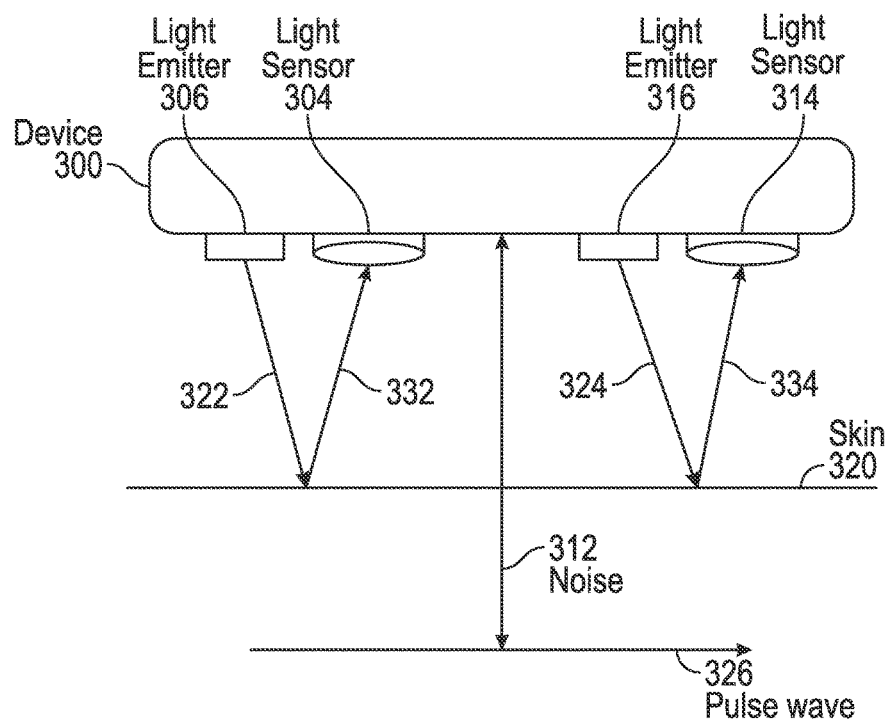

FIG. 3A illustrates a top view and FIG. 3B illustrates a cross-sectional view of an exemplary electronic device including light sensors and light emitters for determining a heart rate signal. A light sensor 304 can be located with a light emitter 306 on a surface of device 300. Additionally, another light sensor 314 can be located or paired with light emitter 316 on a surface of device 300. Device 300 can be situated such that light sensors 304 and 314 and light emitters 306 and 316 are proximate to a skin 320 of a user. For example, device 300 can be held in a user's hand or strapped to a user's wrist, among other possibilities.

Light emitter 306 can generate light 322. Light 322 can be incident on skin 320 and can reflect back to be detected by light sensor 304. A portion of light 322 can be absorbed by skin 320, vasculature, and/or blood, and a portion of light (i.e., light 332) can be reflected back to light sensor 304 located or paired with light emitter 306. Similarly, light emitter 316 can generate light 324. Light 324 can be incident on skin 320 and can reflect back to be detected by light sensor 314. A portion of light 324 can be absorbed by skin 320, vasculature, and/or blood, and a portion of light (i.e., light 334) can be reflected back to light sensor 314 located with light emitter 316. Light 332 and 334 can include information or signals such as a heart rate signal (i.e., PPG signal) due to a blood pulse wave 326. Due to a distance between light sensors 304 and 314 along the direction of the blood pulse wave 326, signal 332 can include a heart rate signal, whereas signal 334 can include a time-shifted heart rate signal. A difference between signal 332 and signal 334 can depend on the distance between light sensors 304 and 314 and the velocity of blood pulse wave 326.

Signals 332 and 334 can include noise 312 due to artifacts resulting from, for example, tilt and/or pull of device 300 relative to skin 320, a user's hair, and/or a user's motion. One way to account for noise 312 can be to locate light sensors 304 and 314 far enough such that noise in signals 332 and 334 may be uncorrelated, but close enough together that PPG signal is corrected in signals 332 and 334. The noise can be mitigated by scaling, multiplying, dividing, adding, and/or subtracting signals 332 and 334.

Figure 3C:
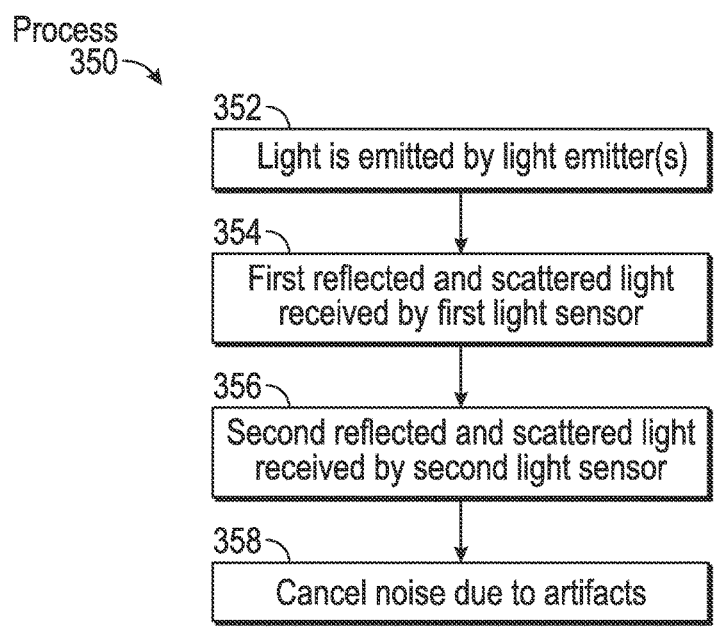
FIG. 3C illustrates a flow diagram for canceling or reducing noise from a measured PPG signal.

FIG. 3C illustrates a flow diagram for canceling or reducing noise from a measured PPG signal. Process 350 can include light emitted from one or more light emitters 306 and 316 (step 352) located on a surface of device 300. Light information 332 can be received by light sensor 304 (step 354), and light information 334 can be received by light sensor 314 (step 356). In some examples, light information 332 and 334 can indicate an amount of light from light emitters 306 and 316 that has been reflected and/or scattered by skin 320, blood, and/or vasculature of the user. In some examples, light information 332 and 334 can indicate an amount of light that has been absorbed by skin 320, blood, and/or vasculature of the user.

Based on light information 332 and light information 334, a heart rate signal can be computed by canceling noise due to artifacts (step 358). For example, light information 334 can be multiplied by a scaling factor and added to light information 332 to obtain the heart rate signal. In some examples, heart rate signal can be computed by merely subtracting or dividing light information 334 from light information 332.

In some examples, light information 332 and 334 can be difficult to determine due to a low signal intensity. To increase the signal intensity or signal strength, the distance between light sensors and light emitters can be reduced or minimized such that light travels the shortest distance. Generally, for a given light emitter and light sensor pair, the signal strength decreases with increasing separation distance between the light emitter and light sensor. On the other hand, the perfusion index generally increases with increasing separation distance between the light emitter and the light sensor. A higher perfusion index can correlate to better rejection of artifacts caused by, for example, motion. Therefore, shorter separation distances between a light emitter and a light sensor can favor high PPG signal strength, while longer separation distances can favor high perfusion index (e.g., motion performance). That is, a trade-off can exist making it difficult to optimize separation distance for particular user skin/tissue types and usage conditions.

Figure 4A:
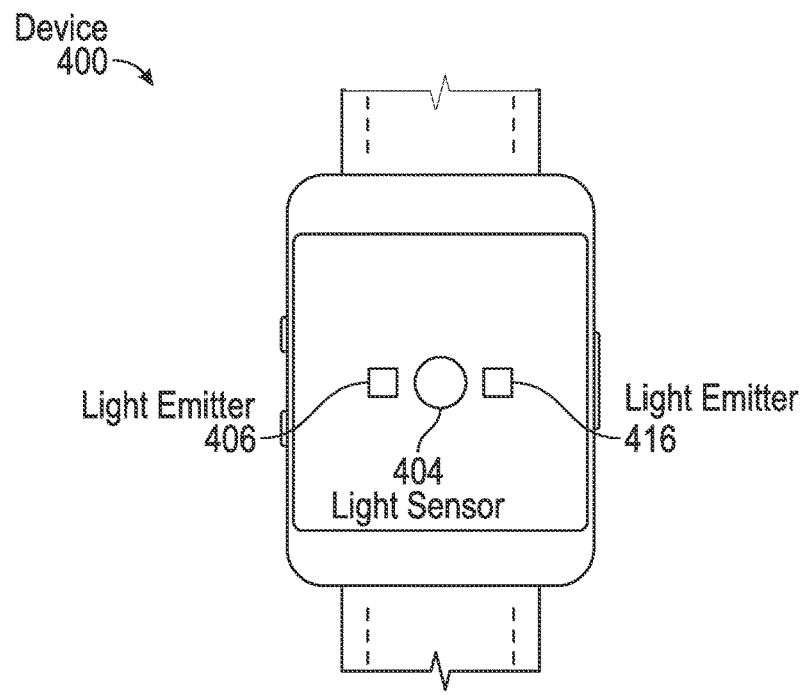
FIG. 4A illustrates a top view and FIG. 4B illustrates a cross-sectional view of an exemplary device with two light paths for determining a heart rate signal according to examples of the disclosure.
Figure 4B:
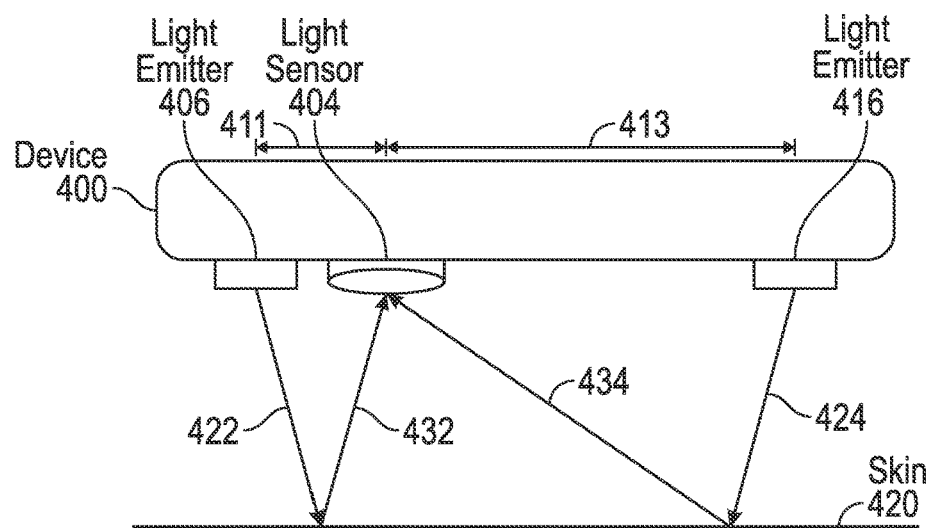

To alleviate the trade-off issue between signal strength and perfusion index, multiple light paths with various distances between light emitter(s) and light sensor(s) can be employed. FIG. 4A illustrates a top view and FIG. 4B illustrates a cross-sectional view of an exemplary device with two light paths for determining a heart rate signal according to examples of the disclosure. Device 400 can include light emitters 406 and 416 and a light sensor 404. Light emitter 406 can have a separation distance 411 from light sensor 404, and light emitter 416 can have a separation distance 413 from light sensor 404.

Light 422 from light emitter 406 can be incident on skin 420 and can reflect back as light 432 to be detected by light sensor 404. Similarly, light 424 from light emitter 416 can be incident on skin 420 and can reflect back as light 434 to be detected by light sensor 404. Separation distance 411 can be small compared to separation distance 413, and as a result, light information 432 can have a higher PPG signal strength than light information 434. Light information 432 can be employed for applications requiring a higher PPG signal strength. Separation distance 413 can be large compared to separation distance 411, and as a result, light information 434 can have a higher perfusion index than light information 432. Light information 434 can be employed for applications requiring a high perfusion index (e.g., motion performance). Due to the different separation distances 411 and 413, light information 432 and 434 can provide various combinations of PPG signals and perfusion index values to allow the device to dynamically select light information for particular user skin types and usage conditions (e.g., sedentary, active motion, etc.).

Figure 5A:
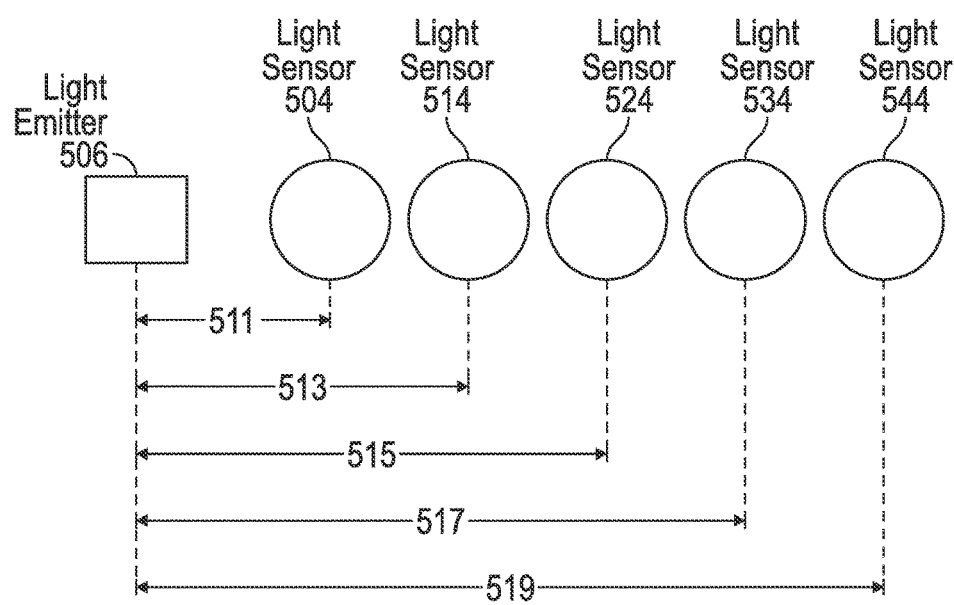
FIG. 5A illustrates multiple light paths for determining a heart rate signal according to examples of the disclosure.

FIG. 5A illustrates multiple light paths for determining a heart rate signal according to examples of the disclosure. For enhanced measurement resolution, more than two light paths can be employed. Multiple light paths can be formed from a light emitter 506 and a plurality of light sensors such as light sensors 504, 514, 524, 534, and 544. Light sensor 504 can have a separation distance 511 from light emitter 506. Light sensor 514 can have a separation distance 513 from light emitter 506. Light sensor 524 can have a separation distance 515 from light emitter 506. Light sensor 534 can have a separation distance 517 from light emitter 506. Light sensor 544 can have a separation distance 519 from light emitter 506. Separation distances 511, 513, 515, 517, and 519 can be different values.

Figure 5B:
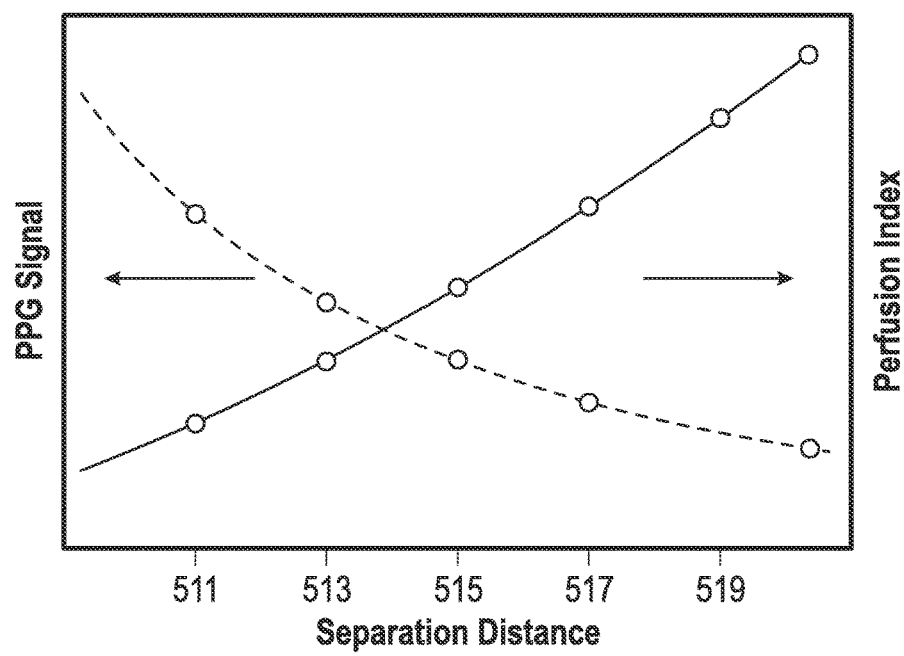
FIG. 5B illustrates a plot of PPG signal strength and perfusion index values for multiple light paths with different separation distances according to examples of the disclosure.

FIG. 5B illustrates a plot of PPG signal strength and perfusion index values for light emitter 506 and light sensors 504, 514, 524, 534, and 544. As shown, an intensity of the PPG signal or signal strength can decrease as the separation distance between a light emitter and a light sensor (i.e., separation distances 511, 513, 515, 517, and 519) increases. On the other hand, the perfusion index value can increase as the separation distance between a light emitter and a light sensor increases.

Information obtained from the multiple light paths can be used both for applications requiring a high PPG signal strength and applications requiring a high perfusion index value. In some examples, information generated from all light paths can be utilized. In some examples, information generated from some, but not all light paths can be utilized. In some examples, the "active" light paths can be dynamically changed based on the application(s), available power, user type, and/or measurement resolution.

Figures 6A, 6B:
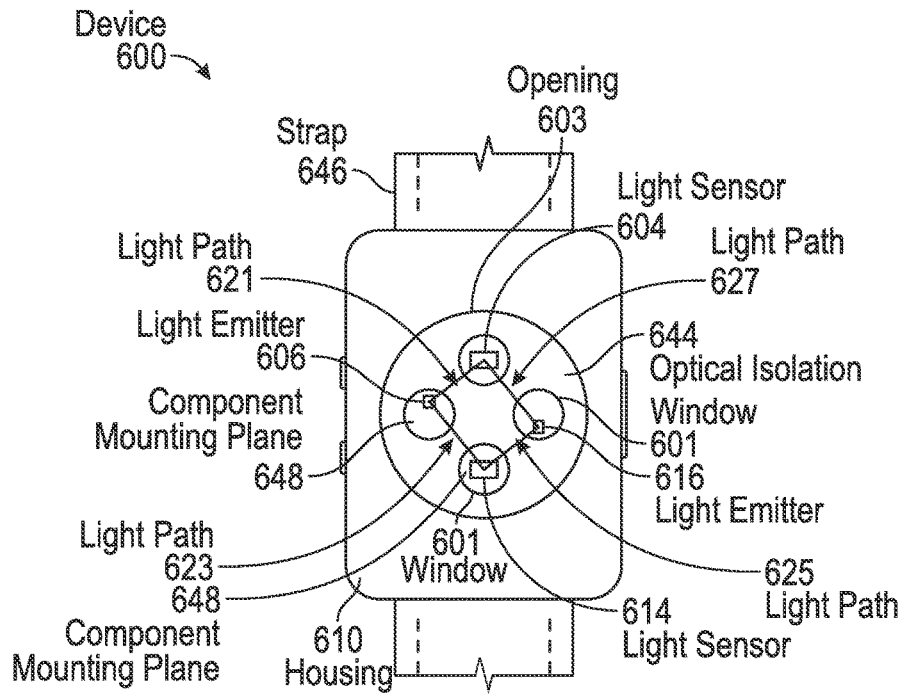
FIG. 6A illustrates a top view of an exemplary electronic device employing multiple light paths for determining a heart rate signal according to examples of the disclosure.
FIG. 6B illustrates a table of exemplary path lengths, relative PPG signal levels, and relative perfusion index values for an exemplary electronic device employing multiple light paths according to examples of the disclosure.
Figure 6C:
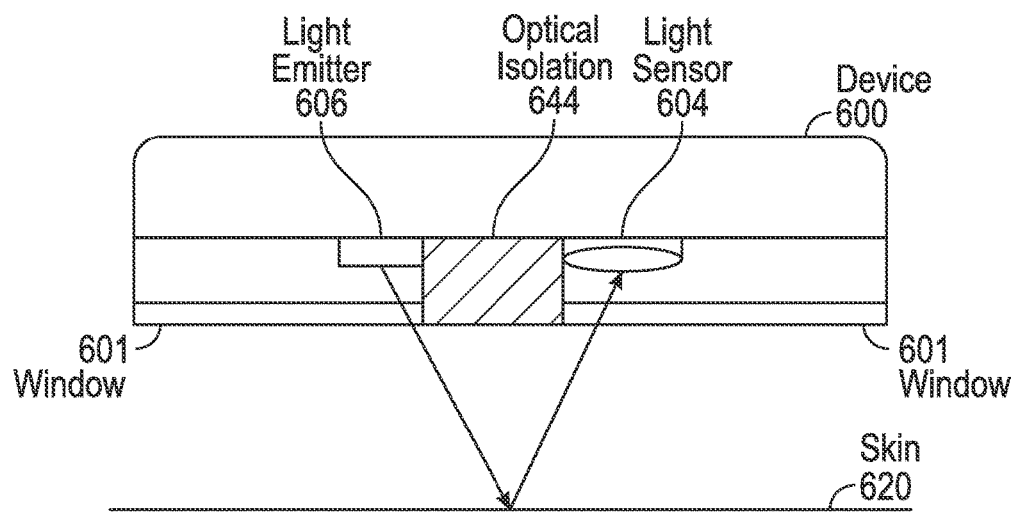
FIG. 6C illustrates a cross-sectional view of an exemplary electronic device employing multiple light paths for determining a heart rate signal according to examples of the disclosure.

FIG. 6A illustrates a top view and FIG. 6C illustrates a cross-sectional view of an exemplary electronic device employing multiple light paths for determining a heart rate signal according to examples of the disclosure. Device 600 can include light emitters 606 and 616 and light sensors 604 and 614 located on a surface of device 600. Light sensors 604 and 614 can be symmetrically placed, while light emitters 606 and 616 can be asymmetrically placed. Optical isolation 644 can be disposed between light emitters 606 and 616 and light detectors 604 and 614. In some examples, optical isolation 644 can be an opaque material to, for example, reduce parasitic DC light.

Light emitters 606 and 616 and light sensors 604 and 614 can be mounted on or touching component mounting plane 648. In some examples, component mounting plane 648 can be made of an opaque material (e.g., flex). In some examples, component mounting plane 648 can be made of a same material as optical isolation 644.

Device 600 can include windows 601 to protect light emitters 606 and 616 and light sensors 604 and 614. Light emitters 606 and 616, light detectors 604 and 614, optical isolation 644, component mounting plane 648, and windows 601 can be located within an opening 603 of housing 610. In some examples, device 600 can be a wearable device such as a wristwatch, and housing 610 can be coupled to a wrist strap 646.

Light emitters 606 and 616 and light detectors 604 and 614 can be arranged such that there are four light paths with four different separation distances. Light path 621 can be coupled to light emitter 606 and light sensor 604. Light path 623 can be coupled to light emitter 606 and light sensor 614. Light path 625 can be coupled to light emitter 616 and light sensor 614. Light path 627 can be coupled to light emitter 616 and light sensor 604.

FIG. 6B illustrates a table of exemplary path lengths, relative PPG signals levels, and relative perfusion index values for light paths 621, 623, 625, and 627 of device 600 according to examples of the disclosure. As shown, relative PPG signal levels can have higher values for shorter path lengths. For example, light path 625 can have a higher PPG signal of 1.11 than light path 627 with a PPG signal of 0.31 due to the shorter path length (i.e., path length of light path 625 is 4.944 mm, whereas path length of light path 627 is 6.543 mm). For applications that require high PPG signal levels, device 600 can utilize information from light path 625 or light path 621. However, relative perfusion index values can have higher values for longer path lengths. For example, light path 623 can have a higher perfusion index value of 1.23 than light path 621 with a perfusion index value of 1.10 due to the longer path length (e.g., path length of light path 623 is 5.915 mm, whereas path length of light path 621 is 5.444 mm). For applications that require high perfusion index values, device 600 can favor information from light path 623 over information from light path 621. While FIG. 6B illustrates exemplary values for path lengths 621, 623, 625, and 627 along with exemplary PPG signal levels and perfusion index values, examples of the disclosure are not limited to these values.

Figure 6D:
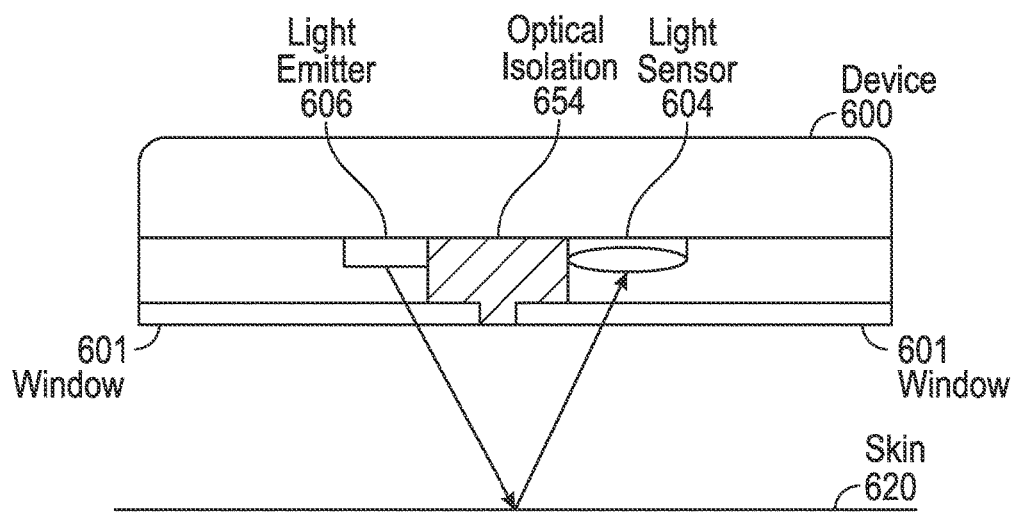
FIGS. 6D-6F illustrate cross-sectional views of exemplary electronic devices employing multiple light paths for determining a heart rate signal according to examples of the disclosure.
Figure 6E:
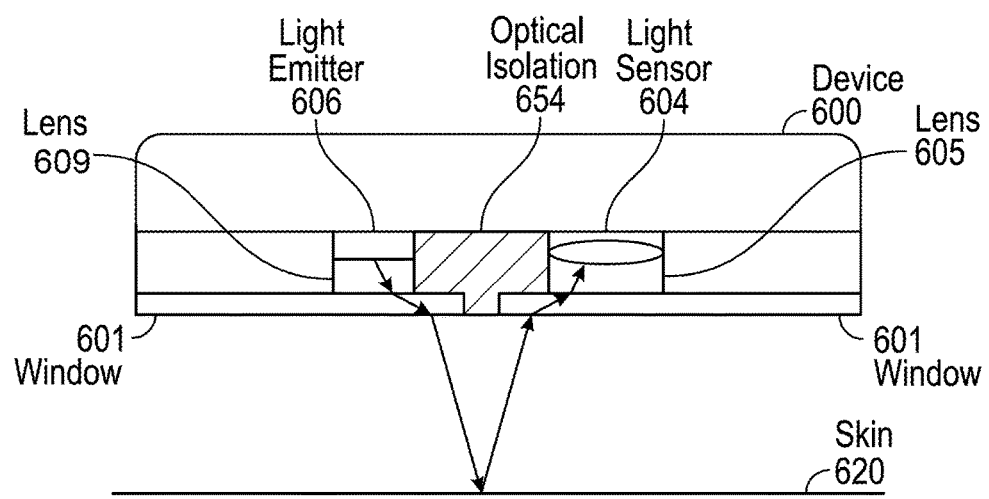
Figure 6F:
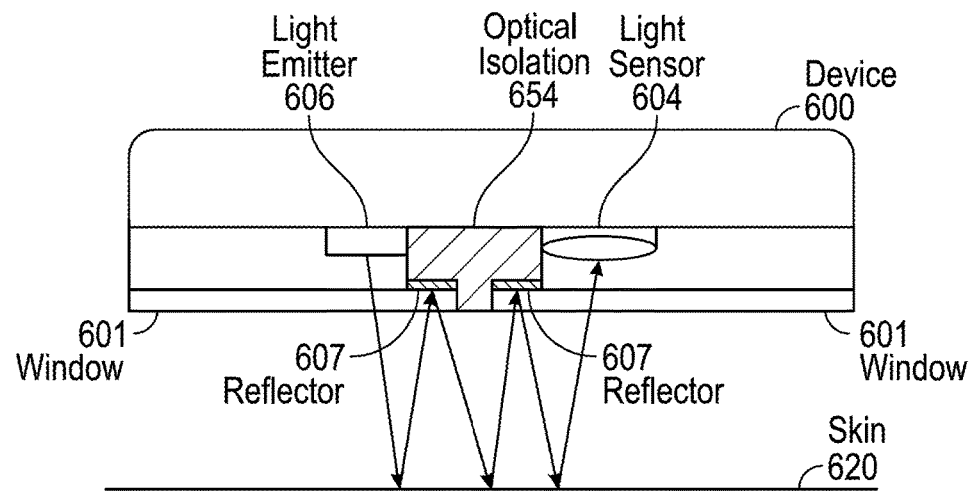

FIGS. 6D-6F illustrate cross-sectional views of exemplary electronic devices employing multiple light paths for determining a heart rate signal according to examples of the disclosure. As shown in FIG. 6D, optical isolation 654 can be designed to improve mechanical stability of device 600 by providing a larger surface area (than optical isolation 644 of FIG. 6C) for windows 601 to rest on and/or adhere to. While optical isolation 654 can provide a larger surface area for windows 601, the light may have to travel a longer distance through skin 620, and as a result, the signal intensity may be reduced. Either the signal quality can be compromised or device 600 can compensate by increasing the power (i.e., battery power consumption) of light emitted from light emitter 606. A lower signal intensity or a higher battery power consumption can degrade the user's experience.

One way to overcome the issues with lower signal intensity and higher power consumption can be illustrated in FIG. 6E. Device 600 can include lens 609 coupled to light emitter 606 and/or lens 605 coupled to light sensor 604. Lens 609 can be any type of lens such as a Fresnel lens or image displacement film (IDF) that steers the light over the optical isolation 644. Lens 605 can be any type of lens such as an IDF or a brightness enhancement film (BEF) that shifts the light into an optical receiving area of light sensor 604. Lens 609 can direct light emitted from light emitter 606 closer to lens 605, and lens 605 can direct light to closer light sensor 604. By employing lenses 609 and/or 605, light may not have to travel a longer distance through skin 620, and as a result, the signal intensity can be recovered.

In some examples, device 600 can include a reflector 607, in addition to or alternatively to lens 609 and 605, as shown in FIG. 6F. Reflector 607 can be formed from any reflective material such as a mirror or a white surface. Light emitted from light emitter 606 can reflect off the surface of skin 620 and be directed back to reflector 607. Such light in the architectures illustrated in FIGS. 6D-6E could be lost or absorbed by optical isolation 654. However, in the architecture illustrated in FIG. 6F, reflector 607 can prevent light loss by reflecting the light back to skin 620, and the light could then be reflected to light sensor 604. In some examples, optical isolation 654 can include any number of reflectors 607. In some examples, one or more windows 601 can include any number of reflectors 607.

Figure 7A:
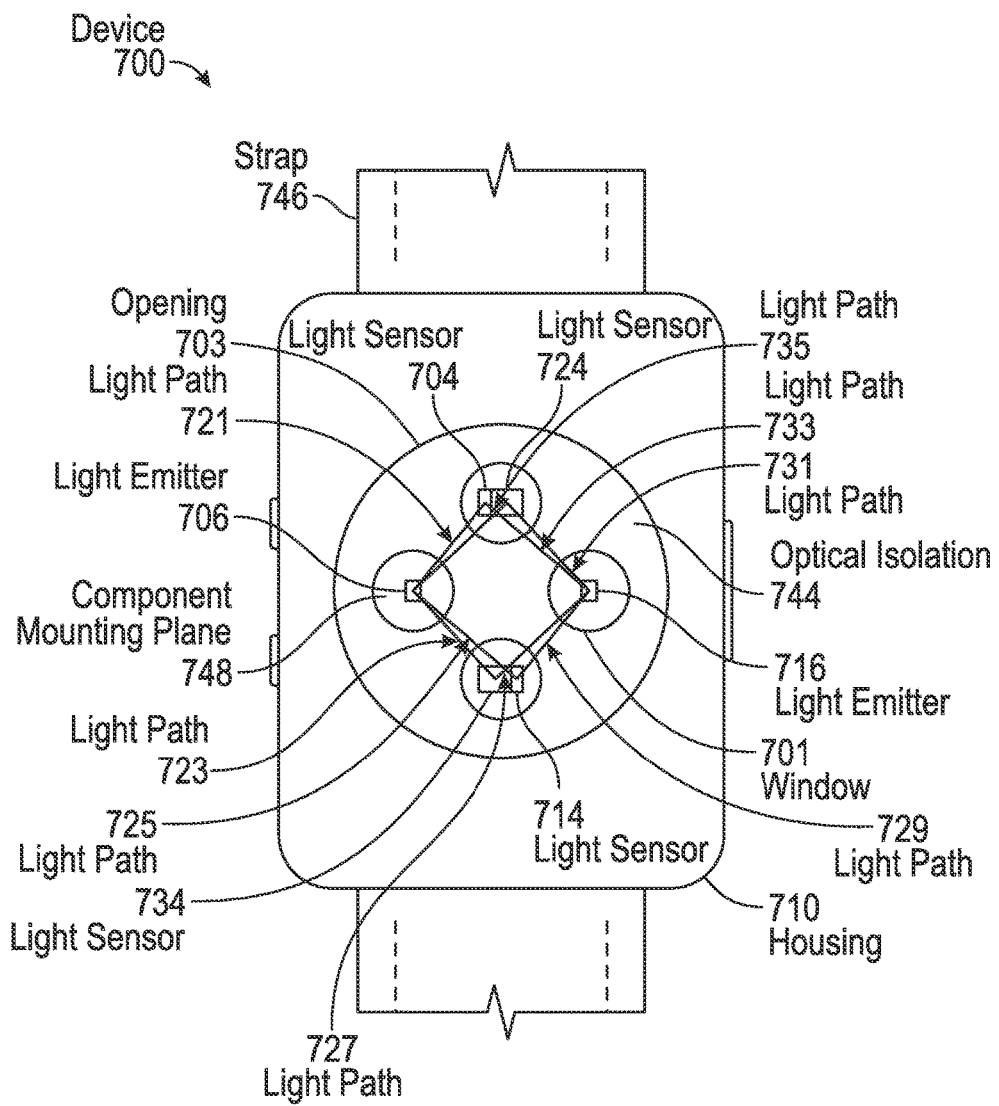
FIG. 7A illustrates a top view of an exemplary electronic device with eight light paths for determining a heart rate signal according to examples of the disclosure.

FIG. 7A illustrates a top view of an exemplary electronic device with multiple light paths for determining a heart rate signal according to examples of the disclosure. Device 700 can include a plurality of light emitters 706 and 716 and a plurality of light sensors 704, 714, 724, and 734 located on a surface of device 700. Optical isolation 744 can be disposed between light emitters 706 and 716 and light sensors 704, 714, 724, and 734 to prevent light mixing. Component mounting plane 748 can be mounted behind light emitters 706 and 716 and light sensors 704, 714, 724, and 734. Windows such as window 701 can be located in front of light emitters 706 and 716 and light sensors 704, 714, 724, and 734 for protection. The plurality of light emitters 706 and 716, plurality of light detectors 704, 714, 724, and 734, optical isolation 744, component mounting plane 748, and windows 701 can be located within an opening 703 of housing 710. In some examples, device 700 can be a wearable device such as a wristwatch, and housing 710 can be coupled to a wrist strap 746.

Although FIG. 7A illustrates two light emitters and four light sensors, any number of light emitters and light sensors can be employed. In some examples, light sensors 704 and 724 can be a single light sensor partitioned into two or more separate sensing regions. Similarly, light sensors 714 and 734 can be a single light sensor partitioned into two or more separate sensing regions. In some examples, optical isolation 744 and/or component mounting plane 748 can be an opaque material. In some examples, one or more of optical isolation 744, component mounting plane 748, and housing 710 can be a same material.

Light emitters 706 and 716 and light sensors 704, 714, 724, and 734 can be arranged such that there are eight light paths with four different path lengths or separation distances. Light path 721 can be coupled to light emitter 706 and light sensor 704. Light path 723 can be coupled to light emitter 706 and light sensor 734. Light path 725 can be coupled to light emitter 706 and light sensor 714. Light path 727 can be coupled to light emitter 716 and light sensor 734. Light path 729 can be coupled to light emitter 716 and light sensor 714. Light path 731 can be coupled to light emitter 716 and light sensor 724. Light path 733 can be coupled to light emitter 716 and light sensor 704. Light path 735 can be coupled to light emitter 706 and light sensor 724.

Light emitters 706 and 716 and light sensors 704, 714, 724, and 734 can be placed such that the separation distances of light paths 721 and 729 (i.e., separation distance d1) are the same, the separation distances of light paths 727 and 735 (i.e., separation distance d2) are the same, the separation distances of light paths 723 and 731 (i.e., separation distance d3) are the same, and the separation distances of light paths 725 and 733 (i.e., separation distance d4) are the same. In some examples, two or more of the light paths can be overlapping light paths. In some examples, two or more of the light paths can be non-overlapping light paths. In some examples, two or more light paths can be co-located light paths. In some examples, two or more light paths can be non-co-located light paths.

An advantage to the multiple light-path architecture illustrated in FIG. 7A can be signal optimization. There can be non-overlapping lights paths such that if there is signal loss in one light path, other light paths can be used for signal redundancy. That is, the device can ensure the existence of a signal by having light paths that collectively span a larger total area. The architecture can mitigate against the risk of having only one light path where signal is either very low or non-existent. A very low or non-existent signal can render a light path ineffective due to, for example, a user's particular physiology where a "quiet" no-signal (or low signal) spot exists. For example, light path 729 can be used for signal redundancy when there is signal loss in light path 721.

Figures 7B, 7C:
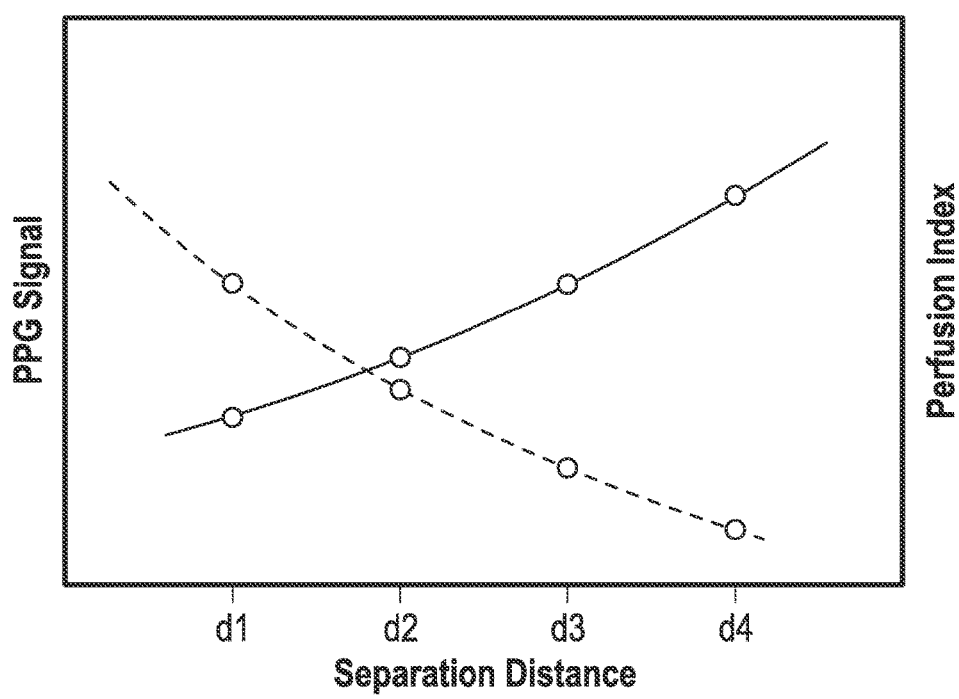
FIG. 7B illustrates a table of light emitter/sensor paths and separation distances for an exemplary electronic device with eight light paths and four separation distances according to examples of the disclosure.
FIG. 7C illustrates a plot of PPG signal strength and perfusion index values for an exemplary architecture with eight light paths and four separation distances according to examples of the disclosure.

FIG. 7B illustrates a table of light emitter/sensor paths and separation distances for an exemplary electronic device with eight light paths and four separation distances according to examples of the disclosure. FIG. 7C illustrates a plot of PPG signal strength and perfusion index values for an exemplary architecture with eight light paths and four separation distances according to examples of the disclosure. As shown, an intensity of the PPG signal can decrease as the separation distance between a light emitter and a light sensor (i.e., separation distances d1, d2, d3, and d4) increases. On the other hand, the perfusion index value can increase as the separation distance between a light emitter and a light sensor increases.

By configuring the light sensors and light emitters such that multiple light paths have a same separation distance, noise due to artifacts such as motion, user hair and user skin can be canceled or reduced. For example, light path 721 and light path 729 can be two different light paths with a same separation distance d1. Due to the separation distance being the same for both light paths, the PPG signal should be the same. However, light path 721 can reflect off a different area of the user's skin, vasculature, and blood than light path 729. Due to the asymmetry of the human skin, vasculature, and blood, light information from light path 721 can be different than light information from light path 729. For example, a user's skin pigmentation in light path 721 can be different than the user's skin pigmentation in light path 729, leading to a different signal for light path 721 and light path 729. Such differences in light information can be used to cancel or reduce noise and/or enhance pulsatile signal quality to determine an accurate PPG signal.

In some examples, light emitters 706 and 716 can be different light sources. Exemplary light sources can include, but are not limited to, light emitting diodes (LEDs), incandescent lights, and fluorescent lights. In some examples, light emitters 706 and 716 can have different emission wavelengths. For example, light emitter 706 can be a green LED and light emitter 716 can be an infrared (IR) LED. A user's blood can effectively absorb light from a green light source, and thus, the light path coupled to light emitter 706 with the shortest separation distance (i.e., light path 721) can be used for a high PPG signal when a user is sedentary, for example. An IR light source can effectively travel further distances through a user's skin than other light sources and as a result, can consume less power. A light path coupled to light emitter 716 (i.e., light paths 727, 729, 731, and 733) can be used when device 700 is operating in a low power mode, for example. In some examples, light emitters 706 and 716 can have different emission intensities.

Figure 7D:
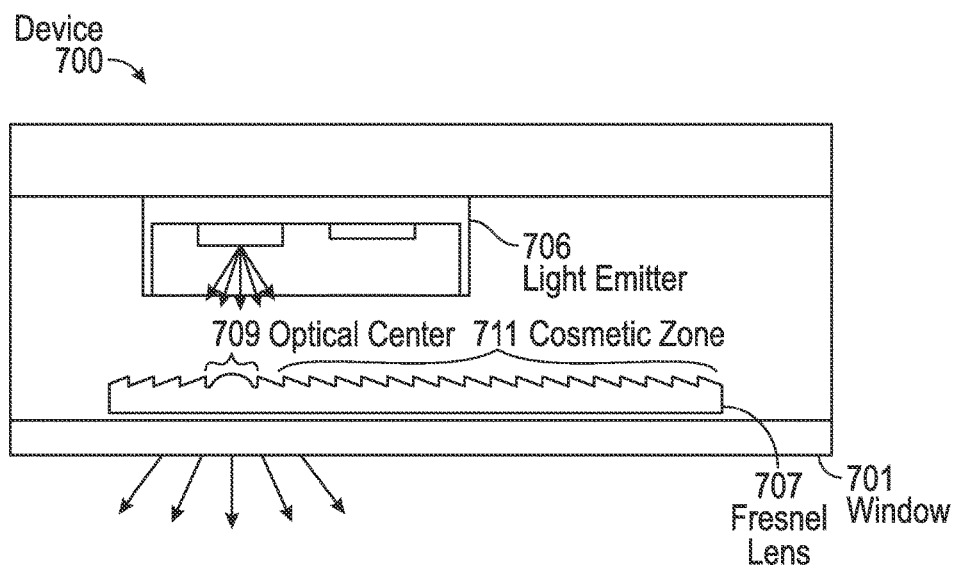
FIGS. 7D-7F illustrate cross-sectional views of exemplary electronic devices employing one or more light paths for determining a heart rate signal according to examples of the disclosure.
Figure 7E:
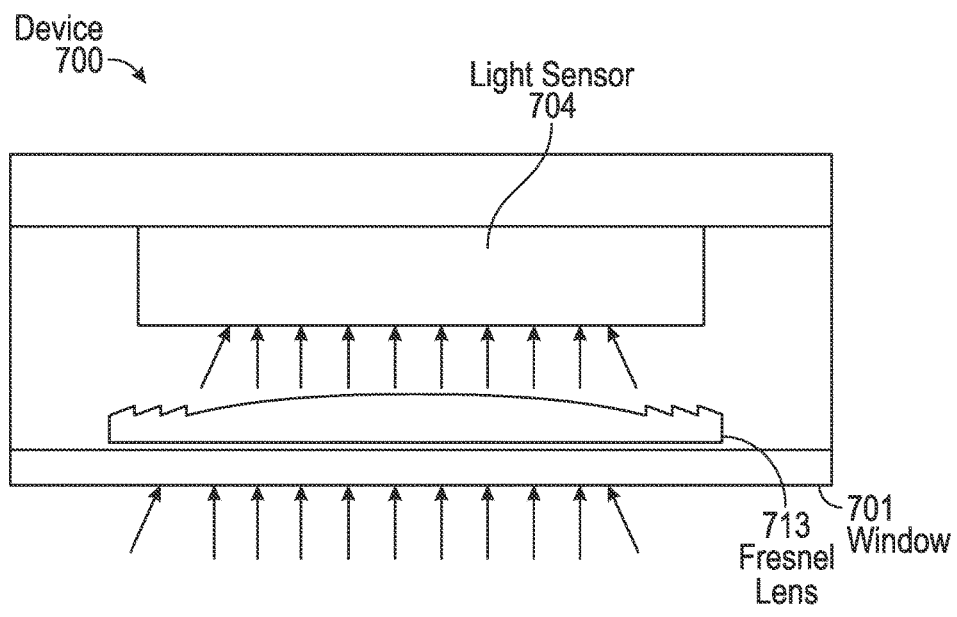
Figure 7F:
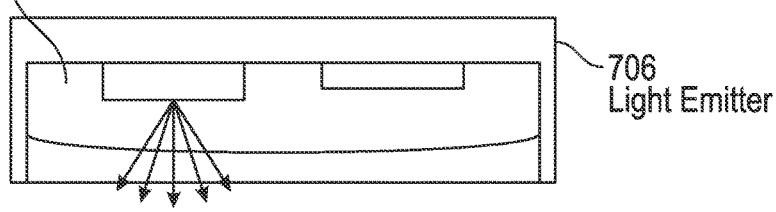

FIGS. 7D-7F illustrate cross-sectional views of exemplary electronic devices employing one or more light paths for determining a heart rate signal according to examples of the disclosure. Device 700 can include window 701 located in front of a component such as light emitter 706 of FIG. 7D and light sensor 704 of FIG. 7E. Window 701 may be transparent, and as a result, the internal components of device 700 may be visible to a user. Since device 700 can include several components and associated wiring, it can be desirable to obscure the components and prevent internal components from being visible to a user's eye. In addition to obscuring the internal components, it may be desirable that the light emitted from light emitter 706 retains its optical power, collection efficiency, beam shape, and collection area so that the intensity of light is unaffected.

To obscure internal components, a lens such as a Fresnel lens 707 can be located between window 701 and light emitter 706, as shown in FIG. 7D. Fresnel lens 707 can have two regions: an optical center 709 and a cosmetic zone 711. Optical center 709 can be placed in substantially a same area or location as light emitter 706 to collimate the emitted light into a smaller beam size. Cosmetic zone 711 can be located in areas outside of optical center 709. The ridges of the cosmetic zone 709 can act to obscure the underlying internal components.

To obscure light sensor 704, a lens such as Fresnel lens 713 can be located between window 701 and light sensor 704, as shown in FIG. 7E. Because light sensor 704 can be a large-area photodiode, shaping of the light field may not be needed, so Fresnel lens 713 may not require an optical center. Instead, Fresnel lens 713 may have one region comprising ridges configured for a cosmetic zone.

The ridge shapes of Fresnel lenses 707 and 713 can be altered to improve obscuration, especially in cosmetic zones. For example, deep and sharp sawtooth patterns can be used for high obscuration needs. Other types of ridge shapes can include rounded cylindrical ridges, asymmetric shapes, and wavy shapes (i.e., ridges that move in and out).

In some examples, the Fresnel lens 707 illustrated in FIG. 7D can be used additionally or alternatively for light collimation. By collimating light, the optical signal efficiency can be improved. Without a lens or similar collimating optical element, emitter light can be directed at an angle away from the light sensor and can be lost. Additionally or alternatively, light can be directed at an angle toward the light sensor, but the angle may be shallow. The shallow angle may prevent the light from penetrating deep enough to reach the signal layers in the skin. This light may contribute only to parasitic, non-signal light. The Fresnel lens 707 can redirect light to directions that otherwise may be lost or enter into the tissue at shallow angles. Such redirected light can be collected instead of being lost and/or can mitigate against parasitic non-signal light, resulting in improved optical signal efficiency.

In some examples, a diffusing agent can be used. Diffusing agent 719 can be surrounding, touching, and/or covering one or more components of light emitter 706. In some examples, diffusing agent 719 can be a resin or epoxy that encapsulates the dies or components and/or wire bonds. Diffusing agent 719 can be used to adjust the angle of the light emitted from light emitter 706. For example, the angle of light emitted from a light emitter without a diffusing agent can be 5° wider than the angle of light emitter from light emitter 706 encapsulated by diffusing agent 719. By narrowing the beam of light emitted, more light can be collected by the lens and/or window resulting in a larger amount of detected light by the light sensor.

In some examples, diffusing agent 719 can have an increased reflectivity for the wavelength or color of emitted light from light emitter 706. For example, if light emitter 706 emits green light, diffusing agent 719 can be made of white $TiO_2$ material to increase the amount of green light reflected back toward the skin. This way, light that would have otherwise been lost can be recycled back and detected by the light detector.

Figure 8:
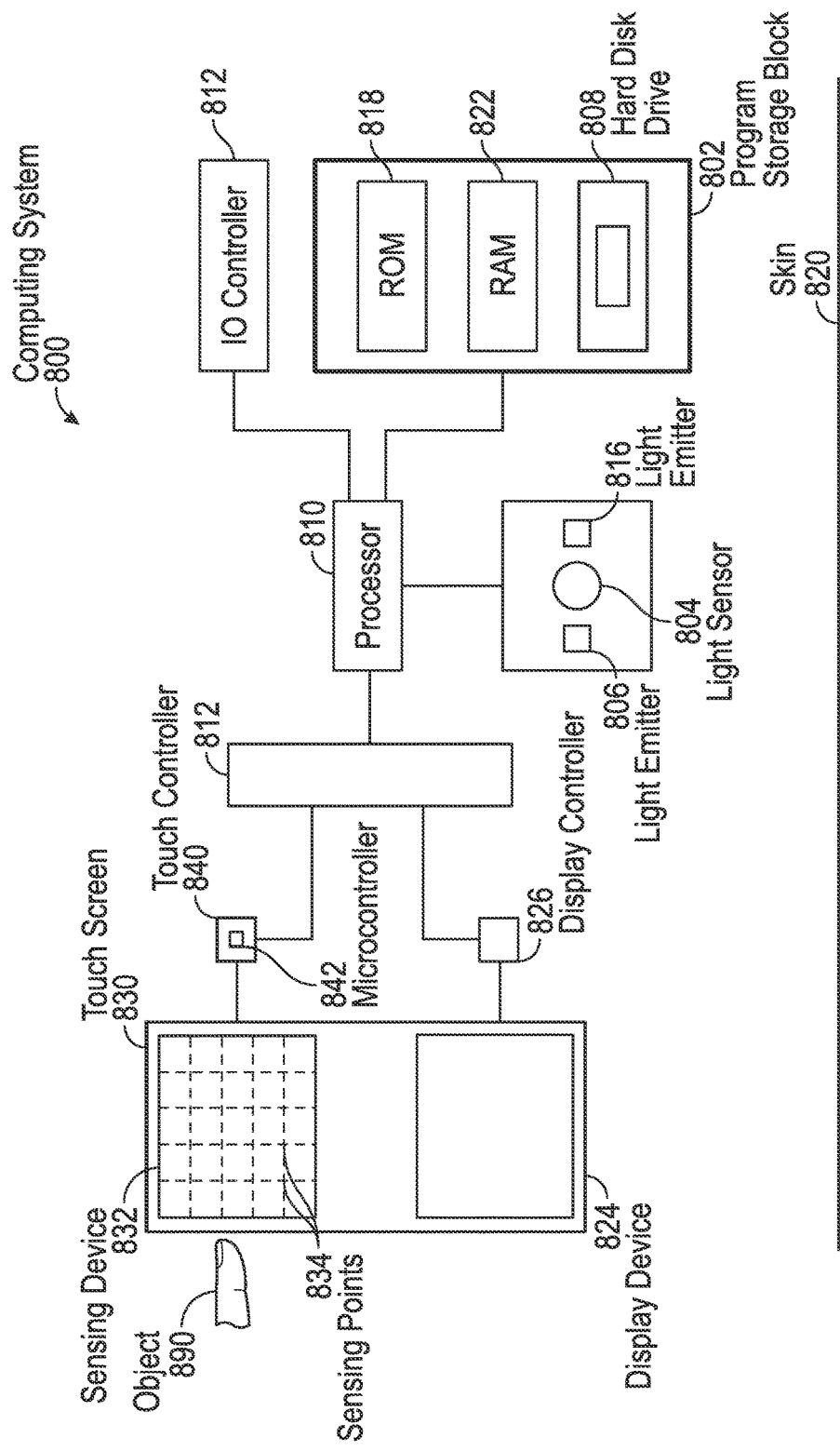
FIG. 8 illustrates an exemplary block diagram of a computing system comprising light emitters and light sensors for measuring a PPG signal according to examples of the disclosure.

FIG. 8 illustrates an exemplary block diagram of a computing system comprising light emitters and light sensors for measuring a PPG signal according to examples of the disclosure. Computing system 800 can correspond to any of the computing devices illustrated in FIGS. 1A-1C. Computing system 800 can include a processor 810 configured to execute instructions and to carry out operations associated with computing system 800. For example, using instructions retrieved from memory, processor 810 can control the reception and manipulation of input and output data between components of computing system 800. Processor 810 can be a single-chip processor or can be implemented with multiple components.

In some examples, processor 810 together with an operating system can operate to execute computer code and produce and use data. The computer code and data can reside within a program storage block 802 that can be operatively coupled to processor 810. Program storage block 802 can generally provide a place to hold data that is being used by computing system 800. Program storage block 802 can be any non-transitory computer-readable storage medium, and can store, for example, history and/or pattern data relating to PPG signal and perfusion index values measured by one or more light sensors such as light sensor 804. By way of example, program storage block 802 can include Read-Only Memory (ROM) 818, Random-Access Memory (RAM) 822, hard disk drive 808 and/or the like. The computer code and data could also reside on a removable storage medium and loaded or installed onto the computing system 800 when needed. Removable storage mediums include, for example, CD-RM, DVD-ROM, Universal Serial Bus (USB), Secure Digital (SD), Compact Flash (CF), Memory Stick, Multi-Media Card (MMC) and a network component.

Computing system 800 can also include an input/output (I/O) controller 812 that can be operatively coupled to processor 810 or it may be a separate component as shown. I/O controller 812 can be configured to control interactions with one or more I/O devices. I/O controller 812 can operate by exchanging data between processor 810 and the I/O devices that desire to communicate with processor 810. The I/O devices and I/O controller 812 can communicate through a data link. The data link can be a one way link or a two way link. In some cases, I/O devices can be connected to I/O controller 812 through wireless connections. By way of example, a data link can correspond to PS/2, USB, Firewire, IR, RF, Bluetooth or the like.

Computing system 800 can include a display device 824 that can be operatively coupled to processor 810. Display device 824 can be a separate component (peripheral device) or can be integrated with processor 810 and program storage block 802 to form a desktop computer (all in one machine), a laptop, handheld or tablet computing device of the like. Display device 824 can be configured to display a graphical user interface (GUI) including perhaps a pointer or cursor as well as other information to the user. By way of example, display device 824 can be any type of display including a liquid crystal display (LCD), an electroluminescent display (ELD), a field emission display (FED), a light emitting diode display (LED), an organic light emitting diode display (OLED) or the like.

Display device 824 can be coupled to display controller 826 that can be coupled to processor 810. Processor 810 can send raw data to display controller 826, and display controller 826 can send signals to display device 824. Data can include voltage levels for a plurality of pixels in display device 824 to project an image. In some examples, processor 810 can be configured to process the raw data.

Computing system 800 can also include a touch screen 830 that can be operatively coupled to processor 810. Touch screen 830 can be a combination of sensing device 832 and display device 824, where the sensing device 832 can be a transparent panel that is positioned in front of display device 824 or integrated with display device 824. In some cases, touch screen 830 can recognize touches and the position and magnitude of touches on its surface. Touch screen 830 can report the touches to processor 810, and processor 810 can interpret the touches in accordance with its programming. For example, processor 810 can perform tap and event gesture parsing and can initiate a wake of the device or powering on one or more components in accordance with a particular touch.

Touch screen 830 can be coupled to a touch controller 840 that can acquire data from touch screen 830 and can supply the acquired data to processor 810. In some cases, touch controller 840 can be configured to send raw data to processor 810, and processor 810 processes the raw data. For example, processor 810 can receive data from touch controller 840 and can determine how to interpret the data. The data can include the coordinates of a touch as well as pressure exerted. In some examples, touch controller 840 can be configured to process raw data itself. That is, touch controller 840 can read signals from sensing points 834 located on sensing device 832 and turn them into data that the processor 810 can understand.

Touch controller 840 can include one or more microcontrollers such as microcontroller 842, each of which can monitor one or more sensing points 834. Microcontroller 842 can, for example, correspond to an application specific integrated circuit (ASIC), which works with firmware to monitor the signals from sensing device 832, process the monitored signals, and report this information to processor 810.

One or both display controller 826 and touch controller 840 can perform filtering and/or conversion processes. Filtering processes can be implemented to reduce a busy data stream to prevent processor 810 from being overloaded with redundant or non-essential data. The conversion processes can be implemented to adjust the raw data before sending or reporting them to processor 810.

In some examples, sensing device 832 is based on capacitance. When two electrically conductive members come close to one another without actually touching, their electric fields can interact to form a capacitance. The first electrically conductive member can be one or more of the sensing points 834, and the second electrically conductive member can be an object 890 such as a finger. As object 890 approaches the surface of touch screen 830, a capacitance can form between object 890 and one or more sensing points 834 in close proximity to object 890. By detecting changes in capacitance at each of the sensing points 834 and noting the position of sensing points 834, touch controller 840 can recognize multiple objects, and determine the location, pressure, direction, speed and acceleration of object 890 as it moves across the touch screen 830. For example, touch controller 890 can determine whether the sensed touch is a finger, tap, or an object covering the surface.

Sensing device 832 can be based on self-capacitance or mutual capacitance. In self-capacitance, each of the sensing points 834 can be provided by an individually charged electrode. As object 890 approaches the surface of the touch screen 830, the object can capacitively couple to those electrodes in close proximity to object 890, thereby stealing charge away from the electrodes. The amount of charge in each of the electrodes can be measured by the touch controller 840 to determine the position of one or more objects when they touch or hover over the touch screen 830. In mutual capacitance, sensing device 832 can include a two layer grid of spatially separated lines or wires, although other configurations are possible. The upper layer can include lines in rows, while the lower layer can include lines in columns (e.g., orthogonal). Sensing points 834 can be provided at the intersections of the rows and columns. During operation, the rows can be charged, and the charge can capacitively couple from the rows to the columns. As object 890 approaches the surface of the touch screen 830, object 890 can capacitively couple to the rows in close proximity to object 890, thereby reducing the charge coupling between the rows and columns. The amount of charge in each of the columns can be measured by touch controller 840 to determine the position of multiple objects when they touch the touch screen 830.

Computing system 800 can also include one or more light emitters such as light emitters 806 and 816 and one or more light sensors such as light sensor 804 proximate to skin 820 of a user. Light emitters 806 and 816 can be configured to generate light, and light sensor 804 can be configured to measure a light reflected or absorbed by skin 820, vasculature, and/or blood of the user. Light sensor 804 can send measured raw data to processor 810, and processor 810 can perform noise cancellation to determine the PPG signal and/or perfusion index. Processor 810 can dynamically activate light emitters and/or light sensors based on an application, user skin type, and usage conditions. In some examples, some light emitters and/or light sensors can be activated, while other light emitters and/or light sensors can be deactivated to conserve power, for example. In some examples, processor 810 can store the raw data and/or processed information in a ROM 818 or RAM 822 for historical tracking or for future diagnostic purposes.

In some examples, the light sensor(s) can measure light information and a processor can determine a PPG signal and/or perfusion index from the reflected, scattered, or absorbed light. Processing of the light information can be performed on the device as well. In some examples, processing of light information need not be performed on the device itself. FIG. 9 illustrates an exemplary configuration in which a device is connected to a host according to examples of the disclosure. Host 910 can be any device external to device 900 including, but not limited to, any of the systems illustrated in FIGS. 1A-1C or a server. Device 900 can be connected to host 910 through communications link 920. Communications link 920 can be any connection including, but not limited to, a wireless connection and a wired connection. Exemplary wireless connections include Wi-Fi, Bluetooth, Wireless Direct, and Infrared. Exemplary wired connections include Universal Serial Bus (USB), FireWire, Thunderbolt, or any connection requiring a physical cable.

In operation, instead of processing light information from the light sensors on the device 900 itself, device 900 can send raw data 930 measured from the light sensors over communications link 920 to host 910. Host 910 can receive raw data 930, and host 910 can process the light information. Processing the light information can include canceling or reducing any noise due to artifacts and determining physiological signals such as a user's heart rate. Host 910 can include algorithms or calibration procedures to account for differences in a user's characteristics affecting PPG signal and perfusion index. Additionally, host 910 can include storage or memory for tracking a PPG signal and perfusion index history for diagnostic purposes. Host 910 can send the processed result 940 or related information back to device 900. Based on the processed result 940, device 900 can notify the user or adjust its operation accordingly. By offloading the processing and/or storage of the light information, device 900 can conserve space and power enabling device 900 to remain small and portable, as space that could otherwise be required for processing logic can be freed up on the device.

In some examples, an electronic device is disclosed. The electronic device may comprise: one or more light emitters configured to generate a plurality of light paths, wherein at least two of the plurality of light paths have separation distances with a predetermined relationship; one or more light sensors configured to detect the at least two light paths having the predetermined relationship; and logic coupled to the one or more light sensors and configured to detect a physiological signal from the at least two light paths. Additionally or alternatively to one or more examples disclosed above, in other examples, the predetermined relationship is a same separation distance. Additionally or alternatively to one or more examples disclosed above, in other examples, the logic is further configured to generate PPG signals and perfusion signals from the detected physiological signal. Additionally or alternatively to one or more examples disclosed above, in other examples, the predetermined relationship is different separation distances. Additionally or alternatively to one or more examples disclosed above, in other examples, the predetermined relationship is overlapping light paths. Additionally or alternatively to one or more examples disclosed above, the predetermined relationship is non-overlapping light paths. Additionally or alternatively to one or more examples disclosed above, in other examples, the predetermined relationship is co-located light paths. Additionally or alternatively to one or more examples disclosed above, in other examples, the predetermined relationship is non-co-located light paths. Additionally or alternatively to one or more examples disclosed above, in other examples, the logic is further configured to reduce noise in the plurality of light paths. Additionally or alternatively to one or more examples disclosed above, in other examples, the electronic device further comprises one or more first lenses disposed on the one or more light emitters. Additionally or alternatively to one or more examples disclosed above, in other examples, at least one of the one or more first lenses is a Fresnel lens or an image displacement film. Additionally or alternatively to one or more examples disclosed above, in other examples, at least one of the one or more first lenses includes an optical center placed in substantially a same location as light emitted from the one or more light emitters. Additionally or alternatively to one or more examples disclosed above, in other examples, the electronic device further comprises one or more second lenses disposed on the one or more light sensors. Additionally or alternatively to one or more examples disclosed above, in other examples, at least one of the one or more second lenses is an image displacement film, a brightness enhancement film, or a Fresnel lens. Additionally or alternatively to one or more examples disclosed above, in other examples, the electronic device further comprises: an optical isolation disposed between the one or more light emitters and the one or more light sensors; and a reflector disposed on at least one of the optical isolation, a window disposed on the one or more light emitters, and a window disposed on the one or more light sensors. Additionally or alternatively to one or more examples disclosed above, in other examples, at least one light sensor is partitioned into a plurality of sensing regions. Additionally or alternatively to one or more examples disclosed above, in other examples, at least two of the one or more light emitters emit light at different wavelengths. Additionally or alternatively to one or more examples disclosed above, in other examples, at least one light emitter is a green light emitting diode and at least one light emitter is an infrared light emitting diode.

In some examples, a method for forming an electronic device including one or more light emitters and one or more light sensors is disclosed. The method may comprise: emitting light from the one or more light emitters to generate a plurality of light paths, wherein at least two of the plurality of light paths have separation distances with a predetermined relationship; receiving light from the one or more light sensors; and determining a physiological signal from the received light. Additionally or alternatively to one or more examples disclosed above, in other examples, the method further comprises dynamically selecting one or more light paths based on at least one of a user characteristic and a usage condition. Additionally or alternatively to one or more examples disclosed above, in other examples, at least two of the plurality of light paths have a same separation distance, the method further comprises canceling or reducing a noise from the at least two of the plurality of light paths with the same separation distance. Additionally or alternatively to one or more examples disclosed above, in other examples, the at least two of the plurality of light paths including a first light path and a second light path, wherein the first light path has a first separation distance and the second light path has a second separation distance, and the first separation distance is shorter than the second separation distance, the method further comprises: determining a first physiological signal from the first light path; and determining a second physiological signal from the second light path. Additionally or alternatively to one or more examples disclosed above, in other examples, the first physiological signal is indicative of a photoplethysmographic signal and the second physiological signal is indicative of a perfusion index. Additionally or alternatively to one or more examples disclosed above, in other examples, the one or more light emitters includes a first set of light emitters and a second set of light emitters, the method further comprising: dynamically activating the first set of light emitters; and dynamically deactivating the second set of light emitters.

Although the disclosed examples have been fully described with reference to the accompanying drawings, it is to be noted that various changes and modifications will become apparent to those skilled in the art. Such changes and modifications are to be understood as being included within the scope of the disclosed examples as defined by the appended claims.

What is claimed is:

1. An electronic device comprising:
   a first light emitter configured to generate a first light to travel a first light path and a second light to travel a second light path, wherein the first light path is in a different direction than the second light path;
   a first window overlaying the first light emitter;
   a second light emitter configured to generate a third light to travel a third light path and a fourth light to travel a fourth light path, wherein the third light path is in a different direction than the fourth light path;
   a second window overlaying the second light emitter, the second window laterally spaced from the first window;
   a first light sensor located a first separation distance from the first light emitter and a second separation distance from the second light emitter, the first separation distance being different from the second separation distance, wherein the first light sensor is configured to detect the first light and generate a first signal indicative of the detected first light, and detect the fourth light and generate a fourth signal indicative of the detected fourth light;
   a third window overlaying the first light sensor;
   a second light sensor located the second separation distance from the first light emitter and the first separation distance from the second light emitter, wherein the second light sensor is configured to detect the second light and generate a second signal indicative of the detected second light, and detect the third light and generate a third signal indicative of the detected third light;
   a fourth window overlaying the second light sensor, the fourth window laterally spaced from the third window; and
   a processor coupled to the first light sensor and the second light sensor, the processor configured to determine a physiological signal from the first signal and the third signal.

2. The electronic device of claim 1, wherein the processor is further configured to generate photoplethysmography (PPG) signals from the physiological signal.

3. The electronic device of claim 1, wherein the processor is further configured to use the second signal and the fourth signal to reduce noise in the first signal and the third signal.

4. The electronic device of claim 1, further comprising a lens, wherein the lens is a Fresnel lens or an image displacement film.

5. The electronic device of claim 1, further comprising a lens, wherein the lens includes an optical center placed in substantially a same location as the first light from the first light emitter.

6. The electronic device of claim 1, further comprising a lens located between the first window and the first light emitter, wherein the lens is an image displacement film, a brightness enhancement film, or a Fresnel lens.

7. The electronic device of claim 1, further comprising:
an optical isolation disposed between the first light emitter and the first light sensor; and
a reflector disposed on the optical isolation.

8. The electronic device of claim 1, wherein the first light sensor is partitioned into a plurality of sensing regions.

9. The electronic device of claim 1, wherein the first light emitter and the second light emitter emit light at different wavelengths.

10. The electronic device of claim 1, wherein the first light emitter is a green light emitting diode and the second light emitter is an infrared light emitting diode.

11. The electronic device of claim 1, further comprising a diffusing agent covering the first light emitter.

12. The electronic device of claim 11, wherein the diffusing agent is made of white $TiO_2$.

13. The electronic device of claim 1, wherein the processor is further configured to generate perfusion index signals from the second signal and the fourth signal.

14. A method for determining a physiological signal from an electronic device, the electronic device including: a first light emitter, a second light emitter, a first light sensor, a second light sensor, a first window, a second window, a third window, a fourth window, and a processor, the method comprising:
emitting first light from the first light emitter through the first window, the first light traveling a first light path, the first window overlaying the first light emitter;
emitting second light from the first light emitter through the first window, the second light traveling a second light path, wherein the first light path is in a different direction than the second light path;
emitting third light from the second light emitter through the second window, the third light traveling a third light path, the second window overlaying the second light emitter, wherein the second window is laterally spaced from the first window;
emitting fourth light from the second light emitter through the second window, the fourth light traveling a fourth light path, wherein the third light path is in a direction different than the fourth light path;
detecting the first light through the third window using the first light sensor and generating a first signal indicative of the detected first light, the third window overlaying the first light sensor;
detecting the fourth light through the third window using the first light sensor and generating a fourth signal indicative of the detected fourth light,
wherein the first light sensor is located a first separation distance from the first light emitter and a second separation distance from the second light emitter, the first separation distance being different from the second separation distance;
detecting the second light through the fourth window using the second light sensor and generating a second signal indicative of the detected second light, the fourth window overlaying the second light sensor, wherein the fourth window is laterally spaced from the third window;
detecting the third light through the fourth window using the second light sensor and generating a third signal indicative of the detected third light,
wherein the second light sensor is located the second separation distance from the first light emitter and the first separation distance from the second light emitter; and
determining the physiological signal from the first signal and the third signal.

15. The method of claim 14, further comprising dynamically selecting the second signal, the fourth signal, or both to include in the determination of the physiological signal, wherein the dynamic selection is based on at least one of a user characteristic and a usage condition.

16. The method of claim 14, the method further comprising canceling or reducing a noise from the first signal and the third signal.

17. The method of claim 14, wherein the physiological signal is a first physiological signal, the method further comprising:
determining a second physiological signal from the second signal.

18. The method of claim 17, wherein the first physiological signal is indicative of a first photoplethysmographic signal with a first associated perfusion index, and the second physiological signal is indicative of a second photoplethysmographic signal with a second associated perfusion index.

19. The method of claim 14, the method further comprising:
dynamically activating the first light emitter; and
dynamically deactivating the second light emitter.

* * * * *